US009585979B2

(12) United States Patent
Long

(10) Patent No.: US 9,585,979 B2
(45) Date of Patent: Mar. 7, 2017

(54) ENVIRONMENTAL SANITIZER AND ODOR REMOVER FOR PURIFICATION OF FOODS, SURFACES, AIR AND WATER WITH DISPOSABLE OZONE GENERATION ELECTRODE, PRESSURE/FLOW ADAPTABLE VENTURI INJECTOR AND AQUEOUS PHASE FILTER DEVICE

(71) Applicant: Veripure, LLC, Green Bay, WI (US)

(72) Inventor: Ronald Bruce Long, Wickenburg, AZ (US)

(73) Assignee: VERIPURE, LLC, Depere, WI (US)

( * ) Notice: Subject to any disclaimer, the term of this patent is extended or adjusted under 35 U.S.C. 154(b) by 194 days.

(21) Appl. No.: 14/486,996

(22) Filed: Sep. 15, 2014

(65) Prior Publication Data

US 2015/0064075 A1 Mar. 5, 2015

Related U.S. Application Data

(60) Continuation of application No. 13/287,626, filed on Nov. 2, 2011, now Pat. No. 8,834,804, which is a
(Continued)

(51) Int. Cl.
*A61L 9/015* (2006.01)
*B01F 5/04* (2006.01)
(Continued)

(52) U.S. Cl.
CPC .............. *A61L 9/015* (2013.01); *A61L 2/183* (2013.01); *A61L 2/20* (2013.01); *A61L 2/202* (2013.01);
(Continued)

(58) Field of Classification Search
None
See application file for complete search history.

(56) References Cited

U.S. PATENT DOCUMENTS 3,421,999 A 1/1969 Corwin
4,383,976 A 5/1983 Notaro
(Continued)

FOREIGN PATENT DOCUMENTS

EP   0 223 411 A   5/1987
GB   1 549 055 A   8/1979
(Continued)

OTHER PUBLICATIONS

Search Report dated Jun. 3, 2015, in corresponding European Application No. 05711262.5, 5 pages.
(Continued)

*Primary Examiner* — Kishor Mayekar
(74) *Attorney, Agent, or Firm* — Foley & Lardner LLP

(57) ABSTRACT

A dielectric assembly for generating ozone includes a positive electrode, a negative electrode, a dielectric for generating the ozone, and a knob adapted to extend outside of a housing into which the dielectric assembly is to be placed. A system is also provided for sanitizing and deodorizing water, food, surfaces and air including a microbiological reduction filter device having an input connected to a water supply, a venturi injector disposed within a housing and connected to an output of the microbiological reduction filter device which generates ozone and mixes the generated ozone with the water, and an electrode assembly comprising a plurality of electrodes, a dielectric for generating the ozone, and a knob extending outside of the housing. The dielectric in a first embodiment and the entire dielectric assembly in a second embodiment can be removed from the housing and replaced in its entirety by the knob.

19 Claims, 9 Drawing Sheets

Related U.S. Application Data division of application No. 12/427,603, filed on Apr. 21, 2009, now Pat. No. 8,377,385, which is a division of application No. 10/832,401, filed on Apr. 27, 2004, now Pat. No. 7,524,466.

(60) Provisional application No. 60/481,867, filed on Jan. 7, 2004.

(51) Int. Cl.

| | | |
|---|---|---|
| *B01F 3/04* | (2006.01) | |
| *C01B 13/11* | (2006.01) | |
| *A61L 2/20* | (2006.01) | |
| *A61L 2/18* | (2006.01) | |
| *A61L 9/01* | (2006.01) | |
| *C02F 1/78* | (2006.01) | |

(52) U.S. Cl.
CPC ............ *A61L 9/01* (2013.01); *B01F 3/04099* (2013.01); *B01F 5/0413* (2013.01); *B01F 5/0428* (2013.01); *C01B 13/11* (2013.01); *C02F 1/78* (2013.01); *A61L 2202/11* (2013.01); *A61L 2209/212* (2013.01); *B01F 2003/04851* (2013.01); *B01F 2003/04943* (2013.01); *B01F 2005/0433* (2013.01); *B01F 2215/008* (2013.01); *C01B 2201/14* (2013.01); *C01B 2201/22* (2013.01); *C01B 2201/30* (2013.01); *C01B 2201/32* (2013.01); *C01B 2201/62* (2013.01); *C01B 2201/70* (2013.01); *C02F 2201/782* (2013.01); *C02F 2201/784* (2013.01); *C02F 2303/02* (2013.01)

(56) References Cited

U.S. PATENT DOCUMENTS

| 4,681,677 | A | 7/1987 | Kuh et al. | |
|---|---|---|---|---|
| 5,106,589 | A | 4/1992 | Conrad | |
| 5,824,274 | A | 10/1998 | Long | |
| 5,871,701 | A | 2/1999 | Long | |
| 6,165,423 | A | 12/2000 | Crosbie | |
| 6,250,324 | B1 | 6/2001 | Conrad et al. | |
| 6,491,879 | B2 | 12/2002 | Conrad | |
| 6,660,172 | B2 | 12/2003 | Koslow | |
| 6,673,248 | B2 | 1/2004 | Chowdhury | |
| 6,685,825 | B1 | 2/2004 | Chang | |
| 2002/0060175 | A1 | 5/2002 | Conrad et al. | |
| 2004/0036185 | A1* | 2/2004 | Garcia | B01F 5/0415 261/76 |
| 2005/0133615 | A1* | 6/2005 | Gopalan | B01F 3/04503 239/88 |

FOREIGN PATENT DOCUMENTS

| WO | WO-97/06879 A | 2/1997 |
|---|---|---|
| WO | WO-97/34643 A | 9/1997 |
| WO | WO-97/37931 A | 10/1997 |
| WO | WO-02/42217 A | 5/2002 |
| WO | WO-2004/018086 | 3/2004 |

OTHER PUBLICATIONS

Notice of Allowance in U.S. Appl. No. 13/287,626 dated May 22, 2014.
Notice of Allowance received in connection with related application, U.S. Appl. No. 12/427,603, dtd Oct. 3, 2012.
Office Action dated Jun. 18, 2008 as received in corresponding U.S. Appl. No. 10/832,401.
Office Action dated Mar. 7, 2012 as received in corresponding U.S. Appl. No. 12/427,603.
Office Action dated Sep. 28, 2011 as received in corresponding U.S. Appl. No. 12/427,603.
US Notice of Allowance dated Dec. 22, 2008 as received in corresponding U.S. Appl. No. 10/832,401.
US Office Action in U.S. Appl. No. 12/427,603 dated Aug. 1, 2011.
US Office Action in U.S. Appl. No. 13/287,626 DTD Nov. 15, 2013.
Written Opinion of the International Searching Authority dated Sep. 13, 2005 as received in corresponding PCT Application No. PCT/US2005/000176, 8 pages.

* cited by examiner

ENVIRONMENTAL SANITIZER AND ODOR REMOVER FOR PURIFICATION OF FOODS, SURFACES, AIR AND WATER WITH DISPOSABLE OZONE GENERATION ELECTRODE, PRESSURE/FLOW ADAPTABLE VENTURI INJECTOR AND AQUEOUS PHASE FILTER DEVICE

CROSS-REFERENCE TO RELATED APPLICATIONS

The present application is a continuation of U.S. patent application Ser. No. 13/287,626, filed Nov. 2, 2011, which is a divisional of U.S. application Ser. No. 12/427,603, filed Apr. 21, 2009, which is a divisional of U.S. application Ser. No. 10/832,401, filed Apr. 27, 2004, which claims priority to U.S. Provisional Application Ser. No. 60/481,867, filed Jan. 7, 2004, the entire contents of all of which are incorporated herein by reference.

FIELD OF THE INVENTION

The present invention relates to the use of ozone together with microbiological barrier filtration as sterilization for point of use purification, sanitization and odor removal for foods, surfaces, articles, water and air. In particular the present invention relates to corona discharge ozone generator and ozone injection and sanitizer dispensing devices configured for such purpose that are easily maintained and economical to manufacture and to operate. Even more particularly, the present invention provides ozone generation dielectric assemblies for use in such a device, each of which is easily and quickly removed, disposed of and replaced without accessing the inside of the housing. The present invention also includes a means of connecting the ozone generation assemblies to the ozone injection device by a simple assembly manifold. Additionally, the present invention includes an ozone injection device featuring replaceable venturi motive flow throats, which permit proper operation under a variety of pressure and flow rate conditions. The present invention also provides a means of utilizing the ozone produced by the generator for controlling odors in the ambient air at point of use as well as remotely from the device with the use of a connecting tube and direct gas phase insertion and dispensing device.

BACKGROUND OF THE INVENTION

Ozone is an allotropic form of oxygen, which is produced in nature by the exposure of oxygen molecules (O2) to ultraviolet light or to the high voltage associated with lightning. Such exposure breaks apart the oxygen molecules into mono-atomic oxygen and recombines a portion of the oxygen atoms and molecules to form ozone (O3). Manmade ozone is created by the passage of dry, ambient air or pure oxygen either past a source of ultraviolet light or through an electrical discharge, commonly called a corona, which is produced by an electric charge between parallel or concentric electrodes separated by a dielectric to prevent a spark discharge. Ozone produced by corona discharge typically is of a higher concentration than ozone produced by ultraviolet light, thus is rendered more useful for oxidation and purification applications such as may be employed for treatment of liquids and surfaces, as well as odor removal for indoor air. The formation of ozone via the corona discharge method has a concurrent formation of nitrous compounds, which, in the presence of moist air, precipitate small amounts of nitric acid inside the ozone generation chambers. Therefore, air dryers producing very low dew point air are typically employed along with the ozone generator to prevent the acid precipitation from fouling dielectrics and reducing ozone production capabilities.

Ozone is recognized as a potent sanitizer for rinsing and treating foods and surfaces in both aqueous and gas phase. It also is a proven water purifier as well. Ozone is a highly reactive oxidizer, the application of which as a sterilizing and preserving agent is well known. It is the most powerful disinfectant commonly available for food sanitizing and for water treatment and is capable of destroying bacteria up to 3,125 times faster than chlorine. Its ability to destroy such bacteria as *E. coli* virtually on contact is well documented as is its effectiveness against such germs as *staphylococcus*, and *salmonella*. In 1997 the United States Food and Drug Administration recognized and approved ozone as a process for sanitizing the surfaces of food. The bottled water industry, together with the US Food and Drug Administration and many state health agencies, which regulate bottled water production, recognize the purification and post-sanitizing efficiency of ozone and specify that an ozone residual in bottled water shall be between 0.1 and 0.4 Parts Per Million. Ozone's ability to minimize microbiological contamination on the surfaces of meat, cheese, eggs, poultry, fruits, vegetables and so forth has been known since the early 20th century. The treatment of foodstuffs with ozone has been successfully applied both in aqueous phase and gas phase. The resulting enhancement to food safety and the extension of shelf life of such items has made ozone a valuable adjunct to modern food processing and storage operations.

More recently, in studies by the Clemson University Department of Dairy Science, ozone has been proven to be a powerful sterilizer and sanitizer of microbiologically contaminated surfaces that have been subjected to a stream of ozonated water. Further recent studies by the Food Science and Nutrition Department of California Polytechnic University, San Luis Obispo, in conjunction with the inventor of the present invention, confirmed that common microbiological contaminants on food surfaces such as total coliforms, *E. coli, E. coli* 0157:H7, *salmonella, listeria, campylobacter, shigella* and *staphylococcus* can be significantly reduced by low level dissolved ozone application ranging from 0.1 to 0.3 Parts Per Million (PPM). Unlike chemical sanitizers, ozone leaves no chemical residue on treated surfaces, thus it is a highly desirable technology for use in large food processing plants as well as in small commercial applications, such as restaurants, and in personal household use for rinsing such items as dishes, cutting boards, utensils, kitchen sponges, meat trays and so forth, as well as foods. While large-scale ozone food sanitizing process systems have become common, there has been no viable ozone-based sanitizing device available for household or small commercial process applications. As the public becomes more aware of the importance of controlling microbiological contamination of food and surfaces, as well as of water, an effective means of applying ozone purification and sanitization that is simple, safe and economical is needed.

Ozone is indiscriminate in its reaction with microbes, therefore a device for applying such low level ozone amounts for aqueous phase food sanitizing must include a means of assurance that the water into which the ozone is injected is microbiologically pure so that there is little or no ozone demand present to reduce the ozone available for sanitizing rinse. Additionally, the ozone must be applied in a manner that thoroughly and reliably dissolves the low level ozone at a range of water pressure and flow rates that may be encountered in the field. The ozone injector would ideally incorporate a reliable means for protecting the ozone generator from water backing up into the generation electrodes. Additionally, the application of gaseous phase ozone for odor control in ambient air, as well as on selected items, would be a desirable feature as an optional use for such a generation device.

An ozone generator for such application as described needs to be simple, economical and convenient to use. Additionally, it needs to produce relatively high concentration of ozone from ambient air capable of maintaining dissolved ozone residuals in a range of 0.1 to 0.4 PPM. Preferably, such a generator would be of simple construction, which requires minimal service and maintenance. A desirable feature of a simple ozone generator would be its capability to function at full capacity without the necessity of drying the air feed to the ozone generation electrodes. Although there have been attempts to create cleanable electrodes, the inevitable buildup of nitric acid combined with ambient dust and similar contaminants in electrode components that are inaccessible makes the long term operation of such devices problematic. A related problem is that the ultimate buildup of dusty, sticky, acidic film which is difficult to remove may increase the dielectric strength of the dielectric over time, reducing the power of the corona, which results in the reduced concentration of ozone produced.

One of the greatest drawbacks of small under-the-counter or countertop ozone systems has been the use of air dryers to prevent the build up of nitric acid on ozone generator dielectrics. Small air dryers for such applications typically have consisted of containers of silica gel, molecular sieve or similar moisture absorbing agents. These agents must be regenerated frequently via the application of high heat. This regeneration necessity contributes to an excessive maintenance task, which is impractical for the average household or small commercial operation. Although automatically regenerating air dryers are available, they are generally too expensive to make such a system practical from a marketing point of view.

Another drawback for previously designed systems has been the method of dissolving ozone in the water. The two primary methods employed have been bubbling or sparging ozone into a container of water or using a venturi injector to draw the ozone into a stream of water. The first of these two methods creates limitations as to the amount of water that can be treated during a given time period since it relies on the complete direct contact of virtually every molecule of water with ozone molecules. This time factor precludes bubbling as a practical method for purifying a continuous stream of water although the technique remains viable when directed to a small container of water. The second method cited, venturi injection, can be highly efficient, but previous attempts to apply ozone have not addressed efficient injection design across a range of pressure and flow rate conditions. The technology requires a very specific pressure differential across the venturi in order for, first, the ozone to be drawn into the water and, second, for the ozone to be thoroughly and violently dissolved in the water for maximum microbiological and oxidative effect. The general function parameters of a venturi-based ozone injection system require carefully controlled pressure factors both upstream and down stream of the injector.

A major limitation of venturi-based ozone systems has been the lack of a downstream faucet or dispenser valve that maintains adequate free flow without creating a backpressure that defeats the ability of the venturi to draw in ozone and dissolve it thoroughly.

Another shortcoming of previous art in the design of small undercounter and countertop ozone systems has been the use of high voltage alternating current transformers, typically producing upwards of 4,000 volts AC. Inasmuch as these transformers must be in close proximity to the ozone generation electrodes, which, in turn, must be in close proximity to the water being treated, hazardous conditions are presented which make such systems unacceptable for household or small commercial applications Alternating current-based ozone systems also cannot be utilized in remote applications, such as emergency water purification or solar powered water purification, without the addition of expensive power converters.

Previous system designs have attempted to utilize low voltage direct current electronics to overcome the hazards associated with high voltage alternating current. However, the electrical design employed transistorized computer chip technology to deliver spiked direct current to an electrical coil, which, in turn, supplied power to the corona producing electrodes. The shortcomings of this design are that the transistor of the chip heats rapidly, which results in the fading of its ability to produce a consistent level of ozone.

SUMMARY OF THE INVENTION

Accordingly, the present invention has an object, among others, to overcome deficiencies in the prior art such as noted above.

The present invention relates to a surface sanitizing and deodorizing device wherein ozone gas is created for aqueous phase applications as well as gaseous phase applications. In a first operational mode, water is employed as a vehicle to deliver ozone gas to the surfaces of foods and the food preparation environment as well other surfaces and articles at the point of use. In a second operational mode of the present invention, ozone in gas phase is delivered to a point of use port for ambient air odor control and for remote gas phase sanitation of foods, articles or surfaces. In a third operational mode, the ozone generation may be turned off, permitting the passage of water that is filtered but not transporting ozone.

In a first aspect, the present invention is directed toward a device for creating ozone that has ozone generation dielectric components which are accessible from outside the device housing and ozone generation dielectric and electrode components which are accessible from outside the housing and which are disposable as a unit.

In a second aspect, the present invention is directed toward the means to channel ozone from the point of generation and to dissolve the ozone in the water utilizing an ozone gas inductor having a replaceable motive throat and to dispense ozone to sanitize foods, surfaces and water.

In a third aspect, the present invention is directed toward a means of providing the option to deodorize air at the point of use environment without altering the integrity of the invention to provide aqueous phase surface sanitization.

In a fourth aspect, the present invention is directed toward a means of utilizing gas phase ozone to treat articles remotely via an extended ozone gas phase transfer device.

In a fifth aspect, the present invention is directed toward a means of pre-treating the water flowing through the invention aqueous channel utilizing microbiological barrier filtration to reduce or eliminate the ozone demand of the water.

In a sixth aspect of the present invention, the filtration components as described above, are separately mounted remote from the ozone generation and injection component housing of the present invention. Connection to the water intake port of the invention is made from the filtered water output port of the filtration or reverse osmosis system. Thus, the present invention permits the application of dissolved ozone for sanitizing of foods in use with pre-existing filtration or reverse osmosis systems.

In a seventh aspect of the present invention, the system water input line may be connected to a 12 volt direct current water pump which will provide the motive force for water to be processed through the system. Power to the system itself may be supplied by any 12-volt direct current source, such as an automotive battery, an automobile cigarette lighter plug receptacle or a solar powered battery. In this embodiment, the present invention may be utilized for remote water purification or for emergency water purification.

In an eighth aspect of the present invention, an alternate embodiment of the present invention, the KX Industries Microbiological reduction filter may be used singularly with the ozone generation and injection device in a counter-top version.

BRIEF DESCRIPTION OF THE DRAWINGS

For better understanding of the invention and additional objects and advantages thereof, reference is made to the following detailed description and accompanying drawing of a preferred embodiment, wherein.

DETAILED DESCRIPTION OF THE INVENTION

Figure 1:
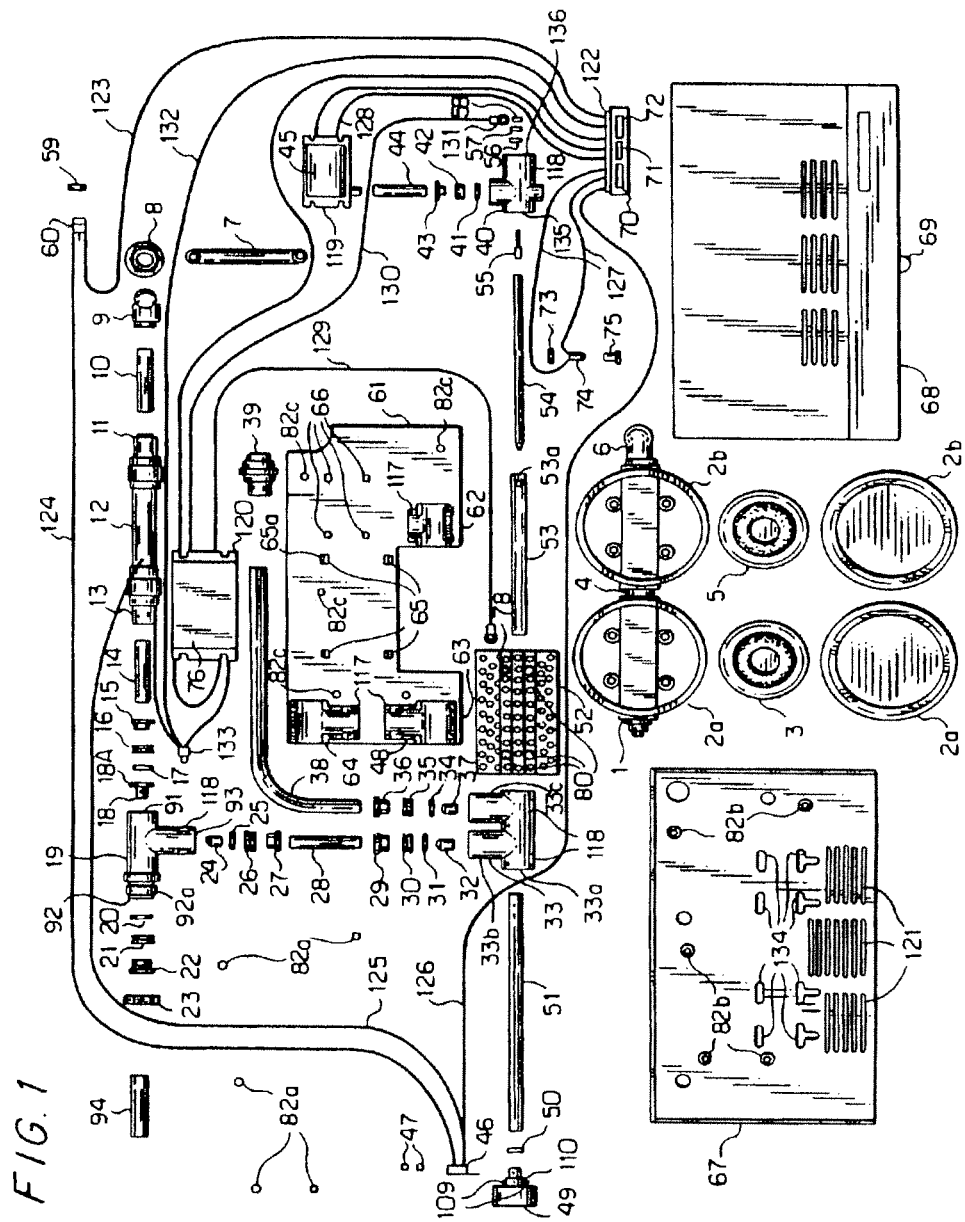
FIG. 1 illustrates the total physical layout of one embodiment of the present invention utilizing the tubular disposable electrode assembly, the air and gas manifolds, and the venturi injector.

According to one operational mode of the present invention, in an aqueous ozonation phase, the water serves as the vehicle to deliver the sanitizing power of the ozone gas to purify the surfaces, and/or remove odors, on foods surfaces and articles. According to another operational mode of the present invention, a gaseous phase, ozone gas is pumped directly into the air through the ozone gas phase delivery port, at which point it may be dispersed directly into the ambient air to oxidize odor molecules in the area of location, or it may be further directed via a tube inserted into the gas phase delivery port and thereby routed and directed to a localized point for odor removal through oxidation of the odor causing molecules in an article (i.e., stinky sneakers) or surface. According to yet another operational mode, an aqueous non-ozonation phase, the water is purified by passing through filters, and exits the system without being mixed with ozone gas.

According to one embodiment of the present invention, in the aqueous phase of operation, water is first filtered through a coarse one-micron-plus carbon particulate filter to remove particulate and chemical contamination. Upon exiting the first filter, the water passes through a submicron or nanofiber microbiological reduction filtration device, specifically including, but not limited to, that (U.S. Pat. No. 6,660,172, incorporated by reference herein in its entirety) by E. E. Koslow and produced by KX Industries, L.P., of 269 South Lambert Road, Orange, Conn. 06477-3502 USA, called the "Matrix Microbiological Barrier" with superior microbiological reduction claims. These capabilities have been certified by the State of California Department of Health Services. The filtration products were certified to meet the following standards: bacterial reduction of 99.9999%, viral reduction of 99.99%, and oocyst (protozoan) reduction of 99.95%. The filtration device meets California-certified microbiological reduction claims. Various technical articles in the literature have recognized the efficacy of combining pre-filtration with ozone post-treatment for controlling cysts such as cryptosporidium and giardia. However, the levels of ozone desirable for point of use food sanitizing, 0.1 to 0.3 PPM, are too low to be effective against such cysts. Therefore, it is desirable to employ a type of filtration that mechanically reduces the presence of cysts, as well as other forms of microbiological ozone demand in the water.

In prior art systems, ozone was used as a primary disinfectant for the water, which reduced the ozone level available for disinfection at the point of use. According to an embodiment of the present invention, the inclusion of a microbiological barrier device reduces or minimizes the ozone demand of the water, making virtually all the ozone carried by the water available for sanitizing foods and surfaces.

The inclusion of the above referenced specific filter as a component also provides benefits by virtue of its ability to halt the flow of water through the entire system of the invention when the filtration capability has reached its design limit. The filter does so by creating a gel that completely plugs the filter cartridge when the organic load, as evidenced by the presence of organic (humic or fulvic) acids on the exterior of the cartridge, exceeds its maximum design flow specification. Another embodiment of the present invention includes pretreatment by carbon and low micron or sub-micron fine filtration, or by reverse osmosis, to create an ozone residual in the treated water to enhance the microbiological integrity of the water for drinking, cooking and other uses.

According to one embodiment of the present invention, ozone is created by a corona discharge electrode, which utilizes pulsed direct current voltage between 9 and 24 volts DC at a frequency between 8 Kilohertz and 35 Kilohertz, the dielectric of which is easily replaced from outside the invention housing, thereby avoiding the necessity of an air dryer. The corona discharge electrode also has a unique interface with a high voltage DC power supply coil that allows compact design and simple assembly.

The present invention contemplates two embodiments of the ozone generation device, a dielectric assembly and an ozone generation electrode dielectric assembly, that are each disposable, replaceable and easily accessible from outside the ozone generator cabinet or housing. Ozone generation electrodes for creating ozone by the corona discharge method generally are comprised of two conductive members separated by a dielectric. Such electrodes sets may be flat, tubular or other shapes. According to one embodiment, the entire dielectric assembly, including the dielectric and two electrodes, is disposable and is easily accessed from outside the housing of the device. According to another embodiment of the present invention, a removable, disposable dielectric is provided that is easily accessed from outside the housing separately from the electrodes.

In prior art systems, the user could potentially be exposed to high voltage inside the device housing when attempting to remove the dielectric for cleaning. One embodiment of the ozone generation electrode according to the present invention solves this problem by providing a replaceable hollow tubular dielectric composed of borosilicate or other heat resistant glass that is open on both ends of the tube. One end of the dielectric is permanently and frictionally encapsulated by a thermoplastic knob that permits the removal, disposal and replacement of the dielectric assembly from outside the invention housing. The dielectric knob additionally secures the electrical integrity of the anodic and cathodic electrode components by pressing the dielectric firmly in to its distal end mounting and holding it in place by means of a screw-in locking method and rubberized o-ring spacer which maintains contact tension, thereby preventing an arcing that might otherwise occur if the dielectric was not firmly in place. According to the present invention, the entire electrode assembly may be manufactured in a variety of dimensions or diameters according to the desired level of ozone output or spatial limiting factors. The ability for the user to remove and dispose of the borosilicate glass dielectric or the dielectric assembly avoids the necessity of attempting to clean nitric acid accumulation from the ozone generation dielectric that could expose the user to possible acid burns or staining of the skin.

The present invention also includes a method of venturi injection and water dispensing which maintains sufficient ozone residual between 0.1 and 0.4 Parts Per Million for assuring microbiological integrity for rinsing surfaces, articles and food items as well as for drinking water. According to an embodiment of the present invention, the motive throat of the venturi injector is replaceable, with each replacement having different internal diameters to allow for optimum ozone induction and mixing under a range of water flow rates and pressures. Additionally, the motive throat insert may be replaced in the instance of calcium carbonate or other mineral accumulation in the motive throat inner diameter, thereby maintaining the functional integrity of the device.

According to one embodiment of the present invention a routing manifold is provided which permits conduit of ozone gas to the venturi injector when subjected to vacuum from the venturi injector, and, alternatively, to a separate dispensing port for gas phase application when the manifold is pressurized by the air pump.

The process system of this invention can be attached to a cold water supply line (not shown) with the use of a saddle tee valve, a piercing valve, slip joint adapter or any similar commonly available undercounter water diverter valves, the application of which is well known in the art. In the countertop version of the present invention, water may be diverted into the present invention by a faucet mounted diverter valve (not shown). Alternatively, water may be supplied to the system by a pump (not shown), preferably one that is capable of delivering at least ½ Gallon Per Minute at a minimum of 15 PSI pressure. Water from the cold water supply line is thereby diverted by way of a flexible hollow tube (not shown), such as is commonly utilized in the art for the communication of water, to the system through a slip lock tube fitting (1) into a first filter sump (2a) containing an internal pre-filtration cartridge (3). The internal pre-filtration cartridge (3) may be one of many commonly available materials designed to remove from water particulate material in the nominal size of one micron or larger and which also may contain a form of either extruded block or granular activated carbon for reduction of chemicals, such as chlorine, chlorine compounds, lead and organic compounds. Alternatively, the pre-filtration cartridge (3) may consist of a five-micron pre-filter. Filter cartridges specifically intended for such utilization are common and well known in the art, therefore will not be described further here.

Following passage through the first filter sump (2a) and pre-filtration cartridge (3), the water exits the sump (2a) through its outflow port via a thread by thread coupler (4) and enters a second sump (2b) and filter cartridge (5). According to one embodiment of the present invention, the filter cartridge (5) is the sub-micron microbiological barrier filter produced by KX Industries, as described above. Other filters can be used such as would be known in the art by one of ordinary skill, including but not limited to a one-micron-absolute carbon block filter. Both sumps are mounted to the neither side of the housing of the present invention by means of screws (not shown) affixed through slots (134) in the housing floor.

According to another embodiment of the present invention, the microbiological reduction filter may be the only filter preceding the ozone injection. The inclusion of this specific filter assures the microbiological integrity of the water by removing microbiological impurities therefrom, which permits a consistent level of dissolved ozone to be available for rinsing of foods, surfaces and articles. The combination of this specific microbiological reduction filter with post ozonation provides advantages over prior art systems.

Figure 4A:
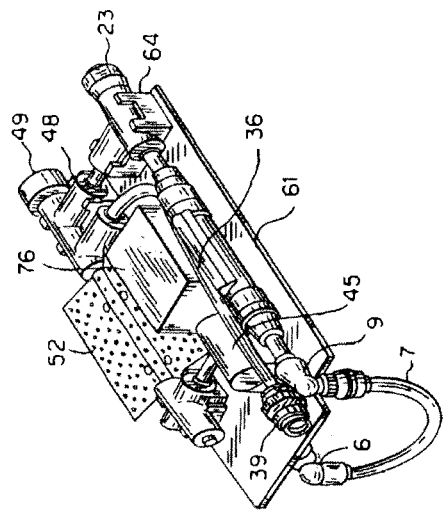
FIGS. 4A-4D illustrate four 3-D views of the present invention, FIG. 4A showing a first perspective view, FIG. 4B showing a second perspective view, FIG. 4C showing a third perspective view, and FIG. 4D showing a fourth perspective view.
Figure 4B:
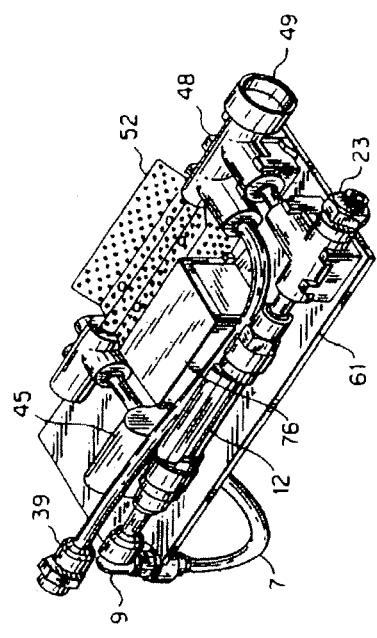
Figure 4D:
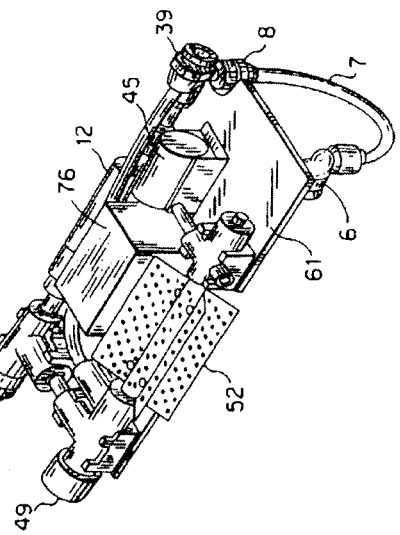
Figure 4C:
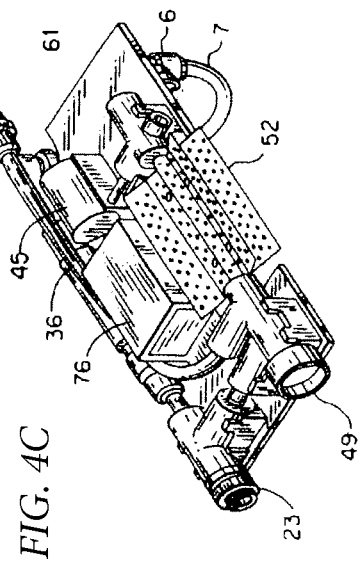

Following a filtration step as discussed above, the filtered water exits the second filter (5) by way of a swiveling elbow slip lock fitting (6) connected to an output of the second sump (2b). One end of a flexible tube (7) composed of food grade plastic which is common in the art, is inserted into the swiveling elbow slip lock fitting (6). According to one embodiment of the present invention, the flexible tube (7) has an inside diameter of ⅛ inch or greater. The distal end of tube (7) is inserted in a first slip lock bulkhead fitting (8), which is affixed through the baseplate 61 of the present invention (see FIG. 4d). The male end of a male elbow fitting (9) is frictionally inserted into the first slip lock bulkhead fitting (8). A first end of a relatively short length of food grade plastic tube (10) is inserted into the other end of elbow fitting (9). A second end of the tube (10) is inserted into a slip lock fitting (11) which communicates directly to, in one preferred embodiment of the present invention, a flow switch (12) such as is common in the art, which accepts the water flow exiting the second filter cartridge (5). The movement of the water flow through the switch (12) creates the motive force to activate the switch (12), thereby providing a means of initiating electrical energy flow from the primary power source.

According to one embodiment of the present invention, the primary power source may be a wall-mounted transformer (not shown) that translates mains voltage alternating current to direct current. Such transformers are commonly available. The translated direct current may range from nine volts DC, according to one embodiment, to a maximum of 24 volts DC. According to another embodiment, the power source for the present invention may be an unregulated direct current battery (not shown) such as is common in automotive or marine applications.

The water flow exits the flow switch (12) through a second slip lock fitting (13) into which is inserted a first end of a second relatively short length of food grade plastic water input tube (14). A second end of the tube (14) is inserted into the water entry port of a venturi injector (19). The design of the venturi injector according to the present invention constitutes a means of mixing ozone gas and water for sanitizing purposes.

Figure 2:
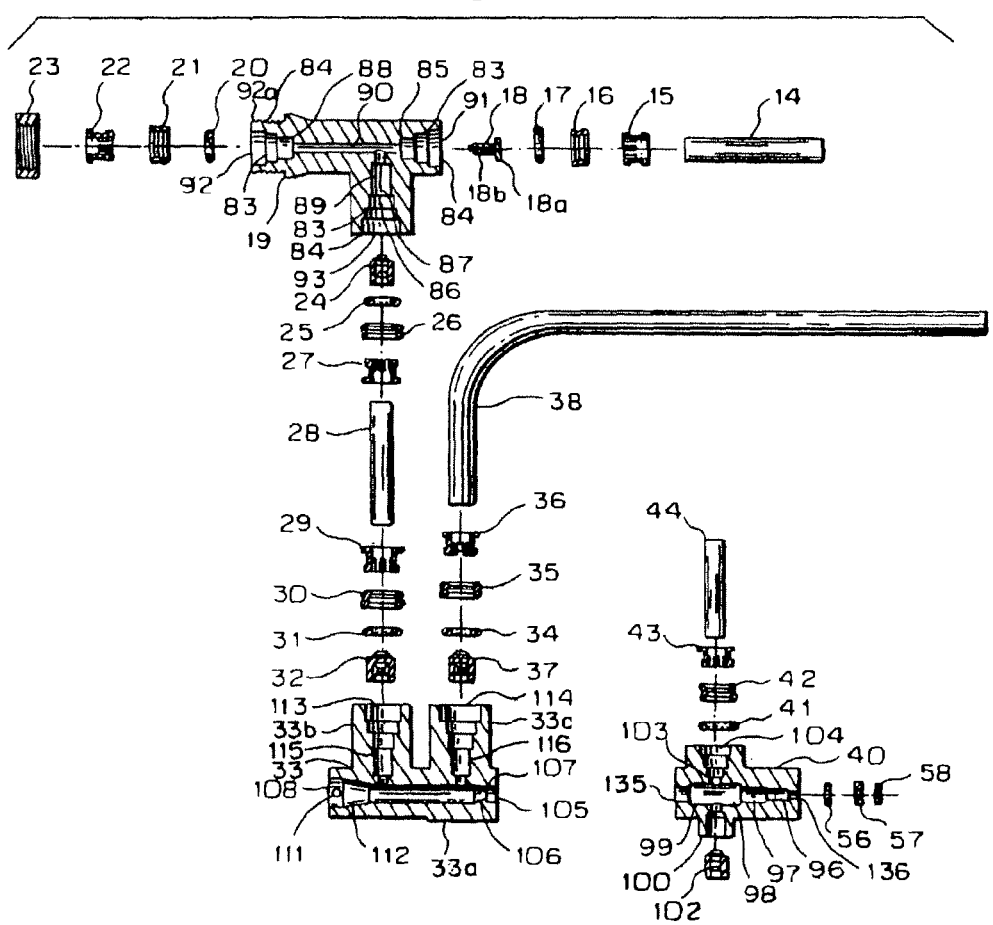
FIG. 2 illustrates the exploded view of one embodiment of the ozone distribution manifold, air intake manifold and venturi injector according to the present invention.
Figure 3:
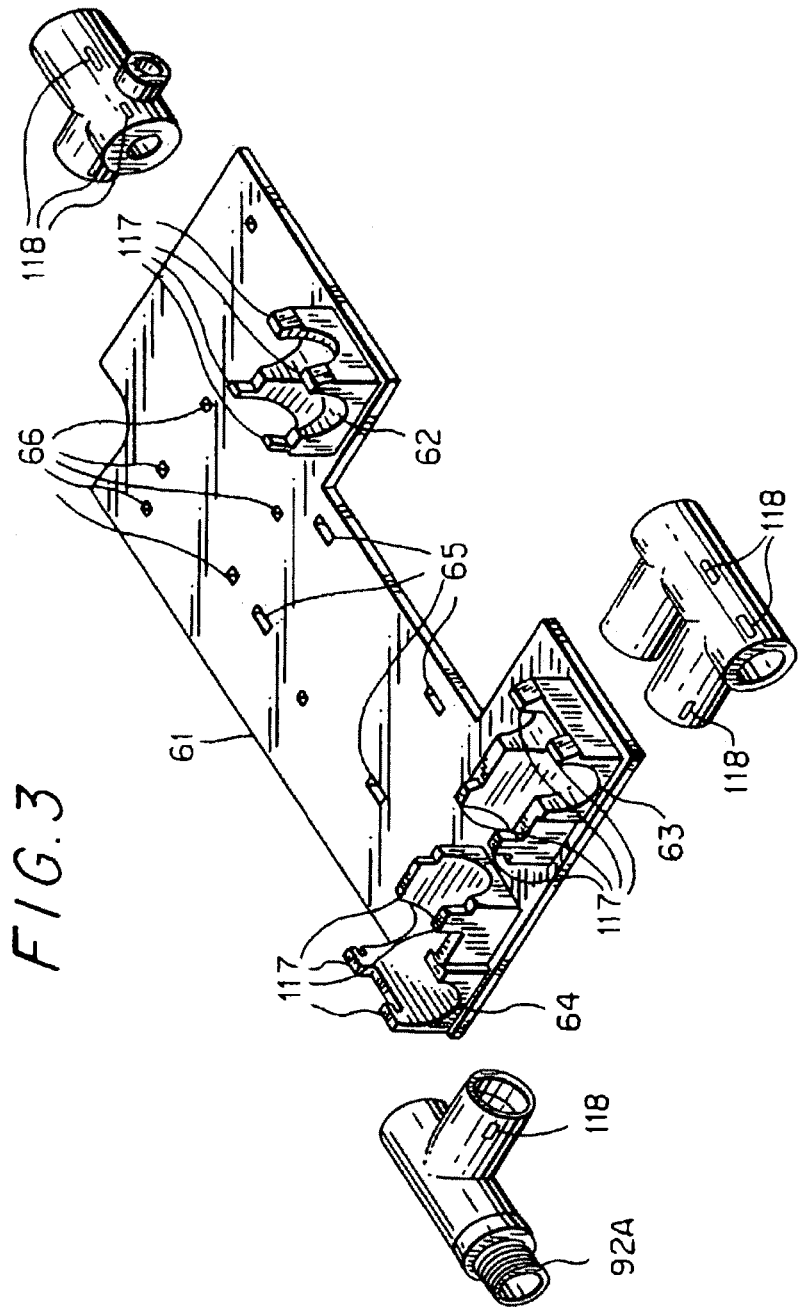
FIG. 3 illustrates a 3-D view of the mounting plate showing the means of snap lock connections on the manifolds and venturi injector according to one embodiment of the present invention.

The venturi injector (19) is formed of a T-shaped pipe. A first aspect of the venturi injector concerns the method of connecting the water transport tubes, water input tube (14) and water exit tube (94) on its two distal ends, water entry port (91) and water exit port (92), respectively, and its' ozone gas transport tube (28) on its' third aperture, gas entry port (93) that is perpendicular to the water flow. The three tube connections each display slip lock connection components comprising a collet locking system. In one embodiment according to the present invention, the collet locking system is a patented collet locking system marketed by John Guest USA, 10 Bloomfield Avenue, Pine Brook, N.J. 07058-0625. As seen in FIG. 2, the three different venture apertures are internally stepped at (83), (84) accordingly to accept the three collet locking system components, i.e., collet (15), (22), and (27), lock ring (16), (21), and (26), and o-ring (17), (20), and (25). The third step (85), (86), and (88) on each venturi aperture, respectively, accepts the ends of plastic tubes (14), (28), and (94), which tubes serve as a stop in each separate instance, and are connected to one another via a T-shaped central tube (90).

The outside diameter portion (92a) of the water exit port (92) is threaded to accommodate threaded nut (23) by which means the venturi injector (19) is affixed to the housing of the present invention through an opening in the housing wall (not shown) which is just large enough to permit insertion of threaded portion (92a) of the venturi injector (19).

The venturi motive throat insert (18), according to one embodiment of the present invention, is seated at the base of the stepped aperture (85), where it is pressed in place frictionally by the second end of the tube (14), which in turn is locked in place by the collet locking system. The top ring end (18a) of the motive throat insert (18) has an outside diameter substantially identical to the outside diameter of the tube (14), while the bottom end (18b) is narrower, having a diameter sized to fit into the central tube (90). Alternative embodiments of the venturi motive throat insert (18), having inside diameters which are produced in different widths and lengths, are interchangeable with one another to accommodate more or less water flow and water pressure according to the application. In the instance of relatively high water pressure, e.g., above about 60 pounds per square inch (PSI), the inner diameter is smaller. In the instance of relatively low water pressure, e.g., less than about 30 PSI, the inner diameter of the venturi motive throat insert (18) is larger. The exact inner motive throat insert diameter may be varied across a wide range of dimensions within the general concept of the present invention, by which accommodation, a single molded or machined venturi injector may be adapted to a range of water flow and water pressure while maintaining its venturi suction and mixing action with the ozone gas.

Figure 5:
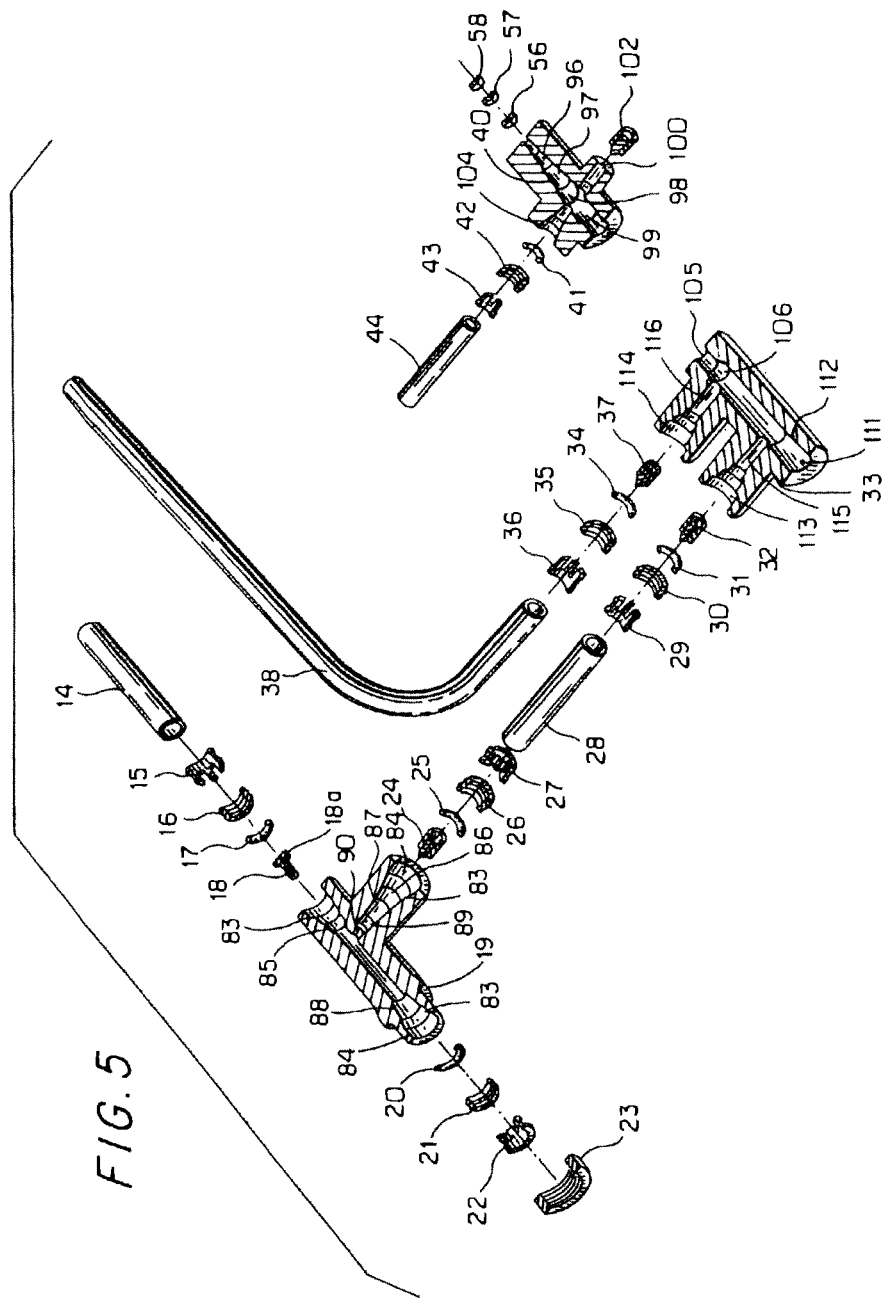
FIG. 5 illustrates the cross sectional perspective of FIG. 2.

An additional aspect of the venturi injector according to the present invention is the means by which water is prevented from entering the ozone gas transport tube and backing up into the ozone generation device. In one embodiment of the present invention, this means is a tubular spring-loaded check valve plunger, one version of which is available from Smart Products, Incorporated, 1710 Ringwood Avenue, San Jose, Calif. 95131 USA. The tubular cartridge check valve (24) is pressed into place into the fourth (87) of four stepped spaces within the gas intake throat (93) of the venturi injector (19) (see e.g., FIG. 2). The fourth step (87) is in communication with the central tube (90), via open space 89 (see FIG. 5). The tubular cartridge check valve (24) is in communication with the open space (89), which permits forward motion of the check valve (24) without hindrance when suction is created through the venturi action. The check valve (24) is pressed in place and held therein by the end of the ozone gas transfer tube (28). The ozone gas transfer tube (28) is in turn held frictionally in place by the collet locking system comprised of lock ring (26), collet (27), and o-ring (25).

In an alternative embodiment of the present invention the check valve (24) of the venturi injector (19) is augmented by means of an electrically actuated valve (not shown) which is normally closed, but which opens when power is supplied to the ozone generator. The electrically actuated valve exit port is in communication with the ozone intake throat of the venturi injector and the electrically actuated valve in-flow port is in communication with the ozone gas transfer tube (28). Electrically actuated valves are common to the art and will not be further described.

The water passes through the length of the venturi injector (19), thereby providing a motive force creating suction at the gas intake port (90) of the venturi injector. The venturi draws in ozone gas mixture and dissolves it in the water stream. The venturi injector (19) of the present invention may be composed of 304 or 316 stainless steel or of a chlorinated polyvinyl chloride thermoplastic such as CPVC® or of any of a variety of ozone resistant materials. The venturi injector (19) may be machined or molded.

The three orifices of the venturi injector (19) are each constructed with female connecting orifice collet locking devices common to the water treatment industry, which are known as "John Guest" fittings. These fittings permit the insertion of tubing on the entrance (91) and exit (92) water flow ports, and the connection of the body of the gas intake port (93) to the ozone generation chamber gas distribution manifold (33). The water thus becomes the vehicle for transporting the sanitizing ozone gas to the surface of foods, surfaces and articles by virtue of its retained ozone residual, to rinse surfaces, articles and foods to reduce microbiological contamination thereof. The ozonized water passes to a dispensing point (not shown) by means of water transport tube (94) which may be a valve or water faucet fixture exhibiting the quality of low resistance, optimally, equal to less than ten percent of the water pressure entering the present invention. By such means and condition, pressure differential across the venturi injector (19) will be approximate ninety percent according to one embodiment of the present invention.

The ozone generation device means according to one embodiment of the present invention comprises a dielectric assembly, which consists of a hollow rod or tube (54), which is the positive electrode, a rod or tube (53), which is the negative electrode, a heat resistant dielectric (51) composed of high temperature resistant material, such as borosilicate glass and a knob (49) by which the dielectric (51) can be removed. According to one embodiment, the positive and negative electrodes (54) and (53) are formed of 316 L stainless steel tubes. According to one embodiment, the dielectric (51) is formed of a tube of such material that is sized to fit and be inserted into the negative electrode (53). The positive electrode (54) is in turn sized to fit and be inserted into the dielectric (51).

The positive electrode (54) of the present invention is attached to a power supply (76) by means of an electrical connector (55). One end of the connector (55) is connected to the power supply (76) and the other end has an outside diameter closely approximating the inside diameter of the dielectric /51\, allowing a relatively tight frictional communication between the connector (55) and the positive electrode (54), which therefore negates the necessity of attachment by solder, or other welded means. The electrical connector (55) is frictionally attached to the positive electrode (54) and inserted through the first end (135) of the air intake manifold (40) and extends towards the second end (136).

In a first aspect, the connector (55) serves the function of providing electrical communication of power to the positive electrode (54). A second aspect of the connector (55) is to align the dielectric (51) substantially in the center of the axial void, or hollow, of the negative electrode (53). At its distal end, the connector (55) is threaded to provide means for attaching, in order, a washer (56), a hexagonal nut (57), an electrical wire end ring connector (131) and a hexagonal locking nut (58). The electrical wire end ring connector (131) is in communication with the positive power lead (130) of the power supply (76) output. The threaded end of the connector (131) is inserted through a step down axial opening (96) in the air intake manifold (40).

The air intake manifold (40), in a first aspect, serves to accommodate the electrical connection and axial centering of the positive electrode (54) within the device dielectric assembly.

In a second aspect, the air intake manifold (40) accommodates the distal end of the dielectric assembly, isolating the positive (54) and negative (53) electrodes from one another, thereby preserving the integrity of the corona discharge.

In a third aspect, the air intake manifold (40) provides a means of holding in place one end of the negative electrode (53), which is inserted frictionally to the point of a chamber stop (98).

In a fourth aspect, the air intake manifold (40) exhibits an air receiving chamber (99) which houses the portion of the one end of the negative electrode (53), which, in one embodiment, is perforated at four quadrant points (perforations (53a)) to permit the flow of air through the corona space extant between the longitudinal annular external surface of the dielectric (51) and the inside longitudinal annular space of the negative electrode (53). The inside diameter of the air receiving chamber (99) according to one embodiment of the present invention, is at least about 15% greater than the outside diameter of the negative electrode (53) to facilitate the free flow of air around and through the perforations (53a).

In fifth aspect of the air intake manifold (40), two pressurized air intake ports (100) and (104) are located opposing one another in direct communication with the receiving chamber (99). A tubular cartridge check valve (102) is frictionally press fit into vacuum air intake port (100). The check valve (102) opens when venturi suction draws air through the corona discharge space of the electrode set when the present invention operates in an aqueous phase. Alternatively, check valve (102) seals under pressurization from the diaphragm air pump (45) through pressurized intake port (104), thereby allowing forced airflow through the corona space. The air pump (45) is in communication with the pressurized air intake port (104) by way of air flow tube (44) frictionally attached to the port (104) by means of the collet locking system composed of the collet (43), lock ring (42) and o-ring (41).

The opposing end of the negative electrode (53) is frictionally encapsulated within the ozone intake port (105) of the ozone distribution manifold (33). A perforated aluminum cooling fin (52), having two opposing halves, is mounted longitudinally. The central line of each half is shaped to accept the outside diameter of the negative electrode (53). The two halves of the cooling fin (52) are fastened together by four screw, washer and nut arrangements (78), (80), one (78) of which cooling fin fastener arrangements serves as the mount point for the negative or ground lead (129) in communication with the power supply (76). The ozone intake throat (106) of the ozone distribution manifold (33) is tapered with the lesser diameter of the taper in communication with the negative electrode end seat (107). The tapered ozone intake throat (106) facilitates the act of insertion of the dielectric (51) and more precisely centers the dielectric within the dielectric assembly. The distal end of the dielectric assembly is inserted within the annular orifice (108) of the ozone distribution manifold (33). The knob shank (110) of the knob (49) includes pegs (109) on its two opposing sides which communicate with the locking channel aspect (111) of the inside diameter of the annular orifice (108) of the ozone distribution manifold (33). Upon insertion of the dielectric assembly into the orifice (108), the elastomer o-ring (50) of the dielectric assembly exerts resistance against the o-ring seat (112) thereby effecting a seal against leakage of ozone gas, in a first aspect, and, in a second aspect, effecting a firm lock to hold the dielectric assembly in operational position. In a third aspect, the fully inserted knob shank (110) is in communication with the activation lever of safety switch (46), which serves to protect the dielectric assembly of the ozone generator against operation without the dielectric in place. Switch (46) communicates with the sidewall of lower housing (67) by means to two mount screws (47).

Figure 6:
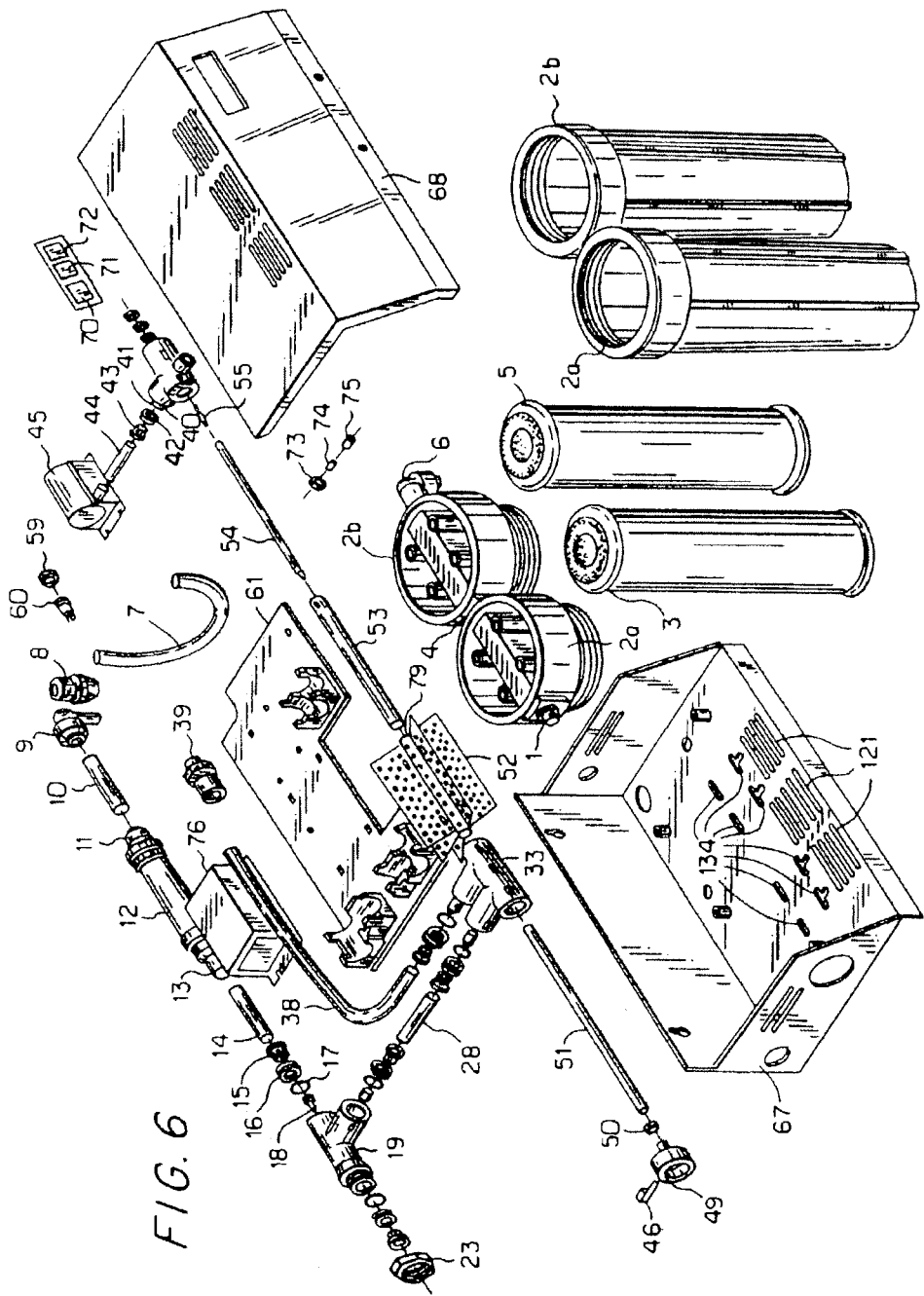
FIG. 6 illustrates a 3-D exploded view of one embodiment of the present invention.
Figure 7:
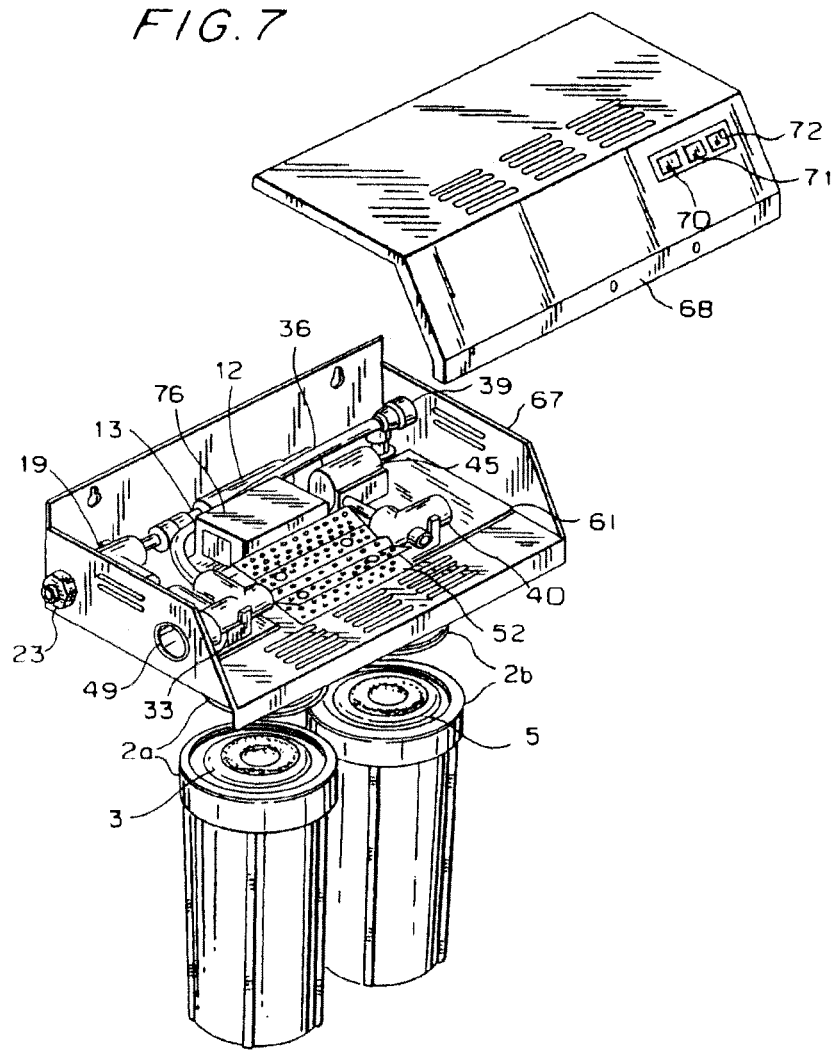
FIG. 7 illustrates an exploded view of one embodiment of the present invention.
Figure 8:
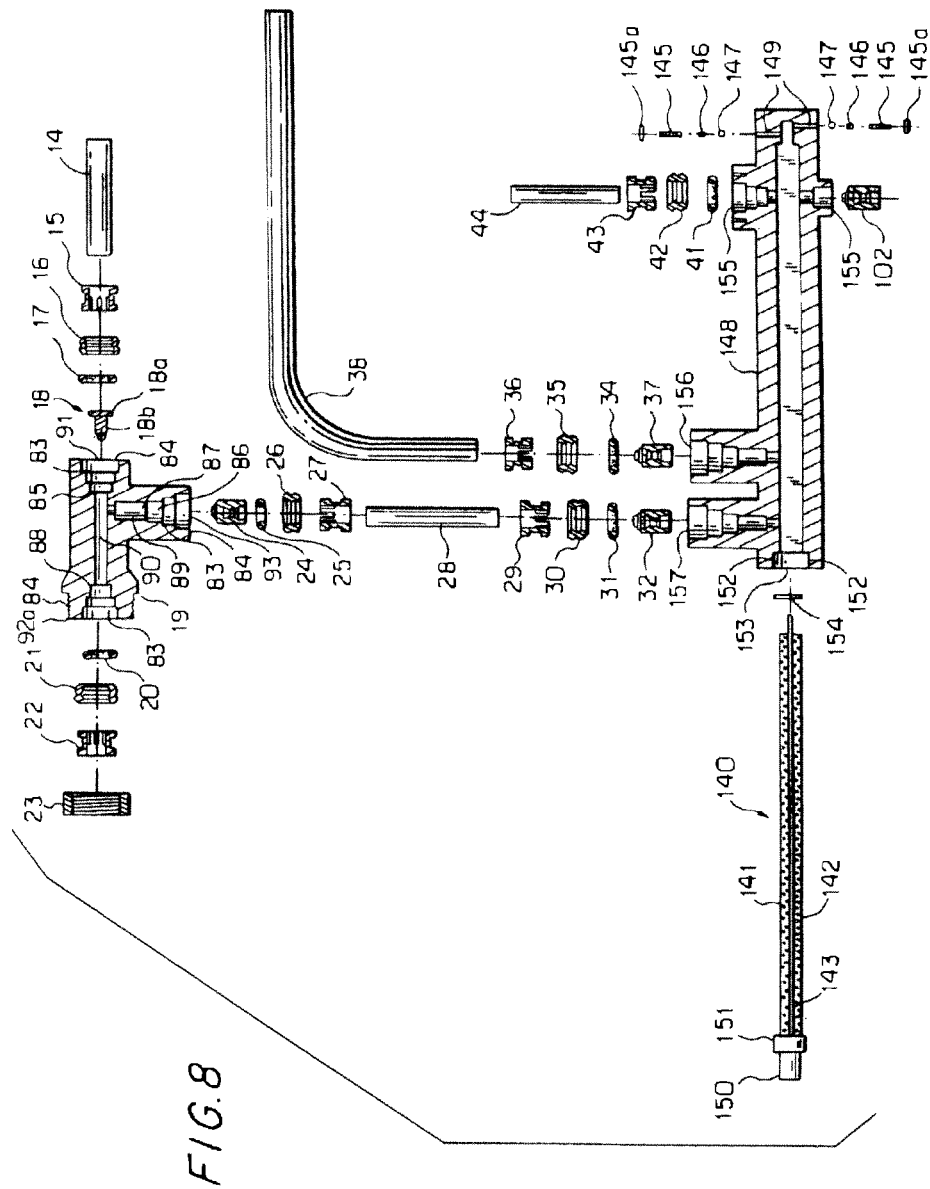
FIG. 8 illustrates an exploded view of the manifold and the venturi injector according to another embodiment of the present invention.
Figure 9:
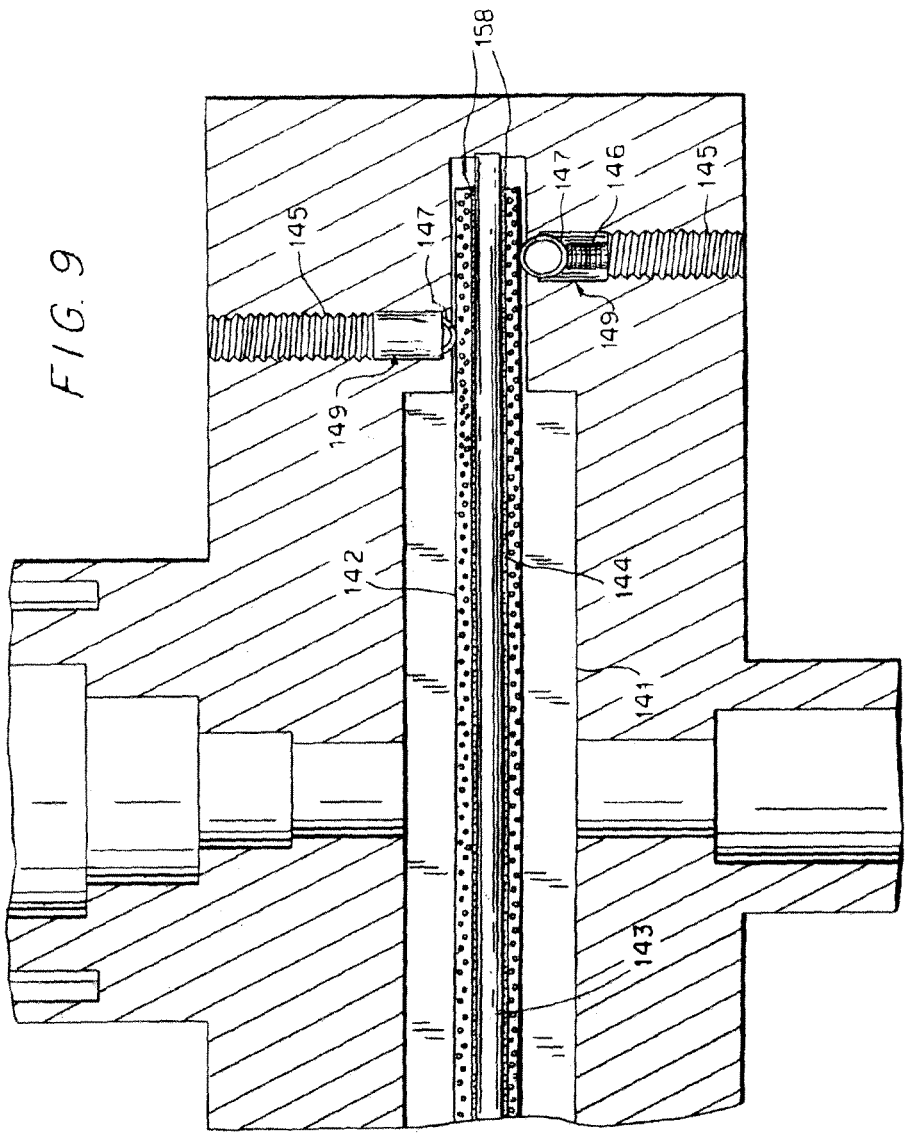
FIG. 9 illustrates an enlarged exploded view of the connection of the dielectric assembly to the power supply according to another embodiment of the present invention.

In another embodiment of the present invention (FIGS. 6, 8 and 9), the ozone generation dielectric assembly is a single unitary structure comprised of positive electrode or anode (141) and a negative electrode or cathode (142) each affixed to the alternate sides Ofa flat dielectric glass plate (143). The anode (141) and cathode (142) consist of a stainless steel mesh permanently affixed to the dielectric glass plate (143) by means of epoxy glue bead (158), which provides the secure communication between dielectric and the two electrodes. The electrodes (141), (142) can have varying dimensions, depending on the desired amount of the ozone to be generated. However, according to one embodiment of the present invention, the electrodes are each about 6" long, ½" wide and about ½₀" thick. The glass plate of the dielectric (143) is slightly larger that the dimensions of the electrodes. The epoxy bead (158) runs along the entire periphery, that is, along the four sides, of the anode (141) and cathode (142). The epoxy bead (157) thus further serves as a means to raise the two opposing electrodes off of the dielectric, thereby providing a dielectric gap (144) within the space created by the bead, between the electrodes and the dielectric, which permits the flow of air or oxygen to pass between electrodes and the dielectric. Other methods of attaching the electrodes to the dielectric while providing the dielectric gap to permit air or oxygen to pass between the electrodes and the dielectric, are considered within the skill of the ordinary artisan.

The anode (141) and the cathode (142) are in communication with the power supply (76), and in particular, the positive power lead (130) on the one side and the negative power lead (129) on the other side, by means of threaded pins (145) which are screwed into orifices (149) in the electrode housing (148). The connection to the power supply (76) is not shown in FIG. 8, but is considered within the skill of the ordinary artisan. The distal end of the pins (145) may be adjusted downward to compress a spring (146), which provides tension on the power ball (147), thereby maintaining sufficient pressure to communicate electrical energy to the two different electrodes.

The dielectric assembly (140), comprised of anode, cathode and dielectric is encapsulated on its distal end by a knob (150), which provides means for grasping and removing the entire dielectric assembly from the electrode housing (148). The cap (150) may be made of a thermoplastic material. The entire dielectric assembly (140), thereby, is able to be removed, disposed of and replaced without exposing a person to harm or staining by nitric acid built up on the electrodes. The assembly (140) is held in communication with the aperture of the electrode housing (148) by means of indentations (151) On the cap and corresponding protrusions (152) which communicate in a male/female manner and which hold the electrode assembly (140) in place by friction fit. The aperture (153) is sealed by a flexible gasket (154) composed of a synthetic rubber, such as EPDM, or other ozone resistant material.

In this alternative electrode form, the air intake manifold and the ozone distribution manifold are constructed as a single plastic molded rectangular device comprising the dielectric set housing (148). The material of the housing may be a fluorine-containing synthetic resin, such as KYNAR®, a chlorinated polyvinyl chloride thermoplastic such as CPVC®, or other ozone resistant plastic. The two pressurized air intake ports (155), the gaseous phase ozone distribution port (156), and the aqueous phase ozone distribution port (157) are constructed using the collet locking system as previously described.

According to one embodiment of the present invention, two different ozone gas exit ports accommodate the alternative operating modes for aqueous phase and for gaseous phase ozone application (see e.g., FIG. 2). This is accomplished, according to one embodiment of the present invention, by providing an ozone distribution manifold (33) that is formed of a double T-shaped pipe. The pipe has an ozone distribution arm portion 33(a) extending along a first axis through which the dielectric assembly is inserted, and two leg portions (33b) and (33c) extending in the same direction as one another, perpendicular to the arm portion (33a). The ozone intake port (105) is at one end of the arm portion (33a) and annular orifice (108) is at the other end.

The aqueous phase ozone exit port (113), in the leg portion (33b) of the ozone distribution manifold (33), includes, according to one embodiment of the present invention, a tubular cartridge check valve (32) as means of preventing entry of water into the dielectric assembly of the present invention. The tubular cartridge check valve (32) is frictionally pressed into the lower stepped orifice arrangement (115) of the aqueous phase ozone gas exit port (113). Additional stability for the position of the tubular cartridge check valve (32) is achieved by means of the end of ozone transfer tube (28) being locked in communication with the check valve (32) by means of a collet locking system, including collet (29), lock ring (30), and o-ring (31).

A gas phase ozone exit port (114) is provided in the leg portion (33b) of the ozone distribution manifold (33) that includes a collet locking system, including collet (34), lock ring (35), and o-ring (36). O-ring (36) is in communication with the gas phase ozone channel tube (38). A means of preventing ambient air from being drawn into the ozone distribution manifold (33) during aqueous phase operation is provided by a tubular cartridge check valve (37). The tubular cartridge check valve (37) is frictionally pressed into the lower stepped orifice arrangement (116) of the gas phase ozone gas exit port (114). Additional stability for the position of the tubular cartridge check valve (37) is achieved by means of the end of the gas phase ozone transfer tube (38) being locked in communication with the check valve (37) by means of a collet locking system, including collet (34), lock ring (35), and o-ring (36). The distal end of the gas phase ozone transfer tube (38) is attached by means of a collet locking system (not shown) to a bulkhead fitting (39). The bulkhead fitting 39 is inserted through the wall of the system housing (67). The exterior aperture of the bulk head fitting (39) exhibits a second collet locking system which may be utilized to grasp an exterior ozone gas distribution tube (not shown) which may be of any convenient length for gas phase application of ozone to remote articles or surfaces. It is understood that the present invention also includes an embodiment (not shown) in which the ozone distribution manifold is formed of a single T-shaped pipe, and that this alternative configuration would eliminate the ozone gaseous phase output option.

According to one embodiment of the present invention, a baseplate (61) is provided which may be molded of thermoplastic or other resilient material. The baseplate (61) includes attachment points exhibiting nesting cavities (64), (63), and (62) into which the venturi injector (19), ozone gas distribution manifold (33) and the air intake manifold (40), respectively, are snapped into firm communication. Each nested component (64), (63), and (62) is held in place by a snap lock (117) and notch (118) exhibiting a male/female interface. The base (120) of internal power supply (76) is held in communication with the plane of the baseplate (61) by a quartet of molded snap locks (65), each having a flexible resilient lip (65a) which faces inward to the power supply (76). Similarly, the air pump (45) is held firmly in communication with the plane of the baseplate (61) by a quartet of molded snap locks (66) in configuration to match the perimeter of the lower air pump housing (119).

According to one embodiment of the present invention, the baseplate (61) is mounted within a housing (67) by means of a number of riser pins (82b) that space and support the baseplate (61) off the floor of the housing to permit air circulation throughout the housing (67) by means of slotted openings (121). The baseplate (61) is affixed onto the riser pins (82b) by means of screws (82a) through holes (82c) in the baseplate (61) and into the hollow threaded throats of the riser pins (82b).

According to one embodiment of the present invention, a flat panel touchpad (122), including switches (70), (71), and (72), provides means of switching the mode of operation from aqueous ozonation phase mode to aqueous non-ozonation mode to gaseous phase mode. Touchpad (122) resides at the front panel of housing lid (68), which, according to one embodiment, is locked to the lower panel of the housing (67) by means of a lockscrew (69). Power to the present invention is communicated through a power jack (60), which is affixed to the wall of the invention enclosure and secured by locknut (59). One lead wire (123) communicates from the power jack (60) to the power input connector of the touchpad (122). A second lead wire (124) communicates from the power jack (60) to one side of the safety switch (46). According to one embodiment of the present invention, connected to the distal side of the safety switch (46). A first lead wire (125) communicates to flow switch (12) and continues to touchpad (122) via circuit wire (132) and a second lead wire (126) communicates to a second power input connector of the touchpad (122). An operational status indicator light includes a bulb (74), a bulb cowl (75) and an attachment nut (73) and communicates to the touchpad panel with a lead wire (127). According to one embodiment, a lead wire (128) communicates power from touchpad (122) to air pump (45). Three separate switch functions (70), (71), and (72) communicate with wire leads (127), (132), and (128) respectively. In particular, lead wire (127) connects the bulb (74) to a switch (70), lead wire (132) connects a wire nut (133) for the power supply (76) to the switch (71), and lead wire (128) connects the air pump (45) to the switch (72).

The device according to the present invention, provides means for operating the system in an aqueous ozonation phase mode in which water passed the system through delivers ozone gas to purify objects on which is put; means for operating the system in a gaseous phase mode in which ozone gas is pumped outside the system to oxidize odor molecules in the area in which it is pumped; and means for operating the system in an aqueous non-ozonation phase mode in which water passed through the system is filtered to remove impurities without being mixed with ozone gas. The device according to the present invention, is switched between its three modes of operation, aqueous ozonation phase mode, aqueous non-ozonation mode, and gaseous phase mode, by activation of switches (70), (71), or (72) respectively.

The means for operating the system in an aqueous non-ozonation phase mode includes the filtering device described above with reference to parts 1-6, the venturi injector (19), the water transport tube 94, and related parts described above. The means for operating the system in a gaseous phase mode includes the dielectric assembly, the air intake manifold (40), the ozone distribution manifold (33), the gas phase ozone transfer tube (38) and the bulkhead fitting (39) and related parts described above. The means for operating the system in a aqueous phase mode includes the filtering device described above with reference to parts 1-6, the venturi injector (19), the dielectric assembly, and related parts described above.

The following is a parts list showing the reference numerals for each part described above.

| | |
|---|---|
| 1 | Slip lock tube fitting |
| 2a | First filter sump |
| 2b | Second sump |
| 3 | Internal pre-filtration cartridge |
| 4 | Thread coupler |
| 5 | Filter cartridge |
| 6 | Swiveling elbow slip lock fitting |
| 7 | Flexible tube |
| 8 | Slip lock bulkhead fitting |
| 9 | Male elbow lock tube fitting |
| 10 | Food grade plastic tube |
| 11 | Slip lock fitting |
| 12 | Flow switch |
| 13 | Second slip lock fitting |
| 14 | Food grade plastic water input tube |
| 15 | Collet |
| 16 | Lock ring |
| 17 | O-ring |
| 18 | Venturi motive throat insert |
| 18a | Top ring end |
| 18b | Bottom end |
| 19 | Venturi injector |
| 20 | o-ring |
| 21 | Lock ring |
| 22 | collet |
| 23 | Threaded nut |
| 24 | Tubular cartridge check valve |
| 25 | O-ring |
| 26 | Lock ring |
| 27 | Collet |
| 28 | Ozone gas transport tube |
| 29 | Collet |
| 30 | Lock ring |
| 31 | o-ring |
| 32 | Tubular cartridge check valve |
| 33 | Ozone generation chamber gas distribution manifold |
| 33a | Ozone distribution arm portion |
| 34 | Collet |
| 35 | Lock ring |
| 36 | o-ring |
| 37 | Tubular cartridge check valve |
| 38 | Gas phase ozone channel tube |
| 39 | Bulk head fitting |
| 40 | Air intake manifold |
| 41 | wring |
| 42 | Lock ring |
| 43 | Collet |
| 44 | Air flow tube |
| 45 | Diaphragm air pump |
| 46 | Safety switch |
| 47 | Two mount screws |
| 49 | Knob |
| 50 | Elastomer o-ring of knob/dielectric assembly |
| 51 | Heat resistant dielectric |
| 52 | Perforated aluminum cooling fin |
| 53 | Stainless steel tube (negative electrode) |
| 53a | Perforations |
| 54 | Stainless steel rod or tube (ozone generation device means) (positive electrode) |
| 55 | Electrical connector |
| 56 | Washer |
| 57 | Hexagonal nut |
| 58 | Hexagonal nut |
| 59 | Locknut |
| 60 | Power jack |
| 61 | Baseplate |
| 62 | Nesting cavity |
| 63 | Nesting cavity |
| 64 | Nesting cavity |
| 65 | Quartet of molded snap locks |
| 65a | Resilient lip |
| 66 | Quartet of molded snap locks |
| 67 | Lower housing |
| 67 | Housing |
| 68 | Housing lid |
| 69 | Lockscrew |
| 70 | Switch functions |
| 71 | Switch functions |
| 72 | Switch functions |
| 73 | Attachment ring |
| 74 | Bulb |
| 75 | Bulb cowl |
| 76 | Power supply |
| 78 | Screw, washer, nut arrangement |
| 80 | Cooling fin fastener arrangement |
| 82b | Riser pins |
| 82a | Screws |

-continued

| | |
|---|---|
| 82c | holes |
| 83 | 2nd step |
| 84 | 1st step |
| 85 | Third step aperture |
| 86 | Third step |
| 87 | Fourth of five stepped spaces in gas intake throat |
| 89 | Open space |
| 90 | Central tube |
| 91 | water entry port |
| 92a | Outside diameter portion of water exit port |
| 92 | Water exit port |
| 93 | Gas intake port |
| 94 | Water transport tube |
| 96 | Step down axial opening |
| 98 | Chamber stop |
| 99 | Air receiving chamber |
| 100 | Vacuum air intake port |
| 102 | Tubular cartridge check valve |
| 103 | Pressurized air intake port |
| 104 | Pressurized air intake port |
| 105 | Ozone intake port |
| 106 | Ozone intake throat |
| 107 | Negative electrode end seat |
| 108 | Annular orifice of distribution manifold 33 |
| 109 | Pegs |
| 110 | Knob shank |
| 111 | Locking channel aspect |
| 112 | Orin g seat |
| 113 | Aqueous phase ozone as exit port of distribution manifold 33 |
| 114 | Gas phase ozone exit port |
| 115 | Orifice arrangement of gas exit port 113 |
| 116 | Lower stepped orifice arrangement of gas exit port |
| 117 | Snap lock |
| 118 | Notch |
| 119 | Lower air pump housing |
| 120 | Base |
| 121 | Slotted openings |
| 122 | Flat panel touchpad |
| 123 | Lead wire from 60 to power input connector of 122 |
| 124 | Lead wire from 60 to safety switch 46 |
| 125 | Lead wire from distal side of safety switch 46 to flow switch 12 |
| 126 | Lead wire from distal side of safety switch 46 to 2d power input connector of 122 |
| 127 | Lead wire from bulb to 122 |
| 128 | Lead wire from 122 to air pump 45 |
| 129 | Negative or ground lead |
| 130 | Power lead |
| 131 | Electrical wire end ring connector |
| 131 | Connector |
| 132 | Lead wire |
| 134 | Slots in the housing floor |
| 133 | Wire nut |
| 135 | First end of 40 |
| 136 | Second end of 40 |
| 140 | Entire set |
| 141 | Anode |
| 142 | Cathode |
| 143 | Flat dielectric glass plate |
| 144 | Dielectric gap |
| 145 | Threaded pin |
| 146 | Spring |
| 147 | Power ball |
| 148 | Dielectric assembly housing |
| 149 | Orifice |
| 150 | Thermoplastic knob |
| 151 | Indentation |
| 152 | Protrusions |
| 153 | Aperture |
| 154 | Flexible gaskets |
| 155 | Air intake port |
| 156 | Gas phase ozone distribution port |
| 157 | Aqueous phase ozone distribution port |
| 158 | Epoxy glue bead |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . " or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A venturi injector for mixing a gas with water, the venturi injector comprising:
   a water entry port at a first distal end of the venturi injector into which an end of a water input tube is insertable;
   a water exit port at a second distal end of the venturi injector opposed to said water entry port, and into which a water exit tube is insertable; and
   a gas entry port disposed transverse to the water entry port and the water exit port into which a gas transport tube is insertable,
   wherein the venturi injector is configured such that, when water flows between the water entry port and the water exit port through a central tube, the water provides a motive force creating suction at the gas entry port, which draws in gas through the gas entry port and dissolves the gas in the water flow, and
   wherein at least one of the water entry port, the water exit port, and the gas entry port comprises a stepped aperture having at least three steps, each having successively narrow diameters moving inward from an outside of the venturi injector.

2. The venturi injector of claim 1,
   wherein the water entry port comprises the stepped aperture having at least three steps, each having successively narrow diameters moving inward from an outside of the venturi injector.

3. The venturi injector of claim 2,
   wherein the water exit port comprises a second one of the stepped apertures having at least three steps, each having successively narrow diameters moving inward from an outside of the venturi injector.

4. The venturi injector of claim 3,
   wherein the gas entry port comprises a third one of the stepped apertures having at least three steps, each having successively narrow diameters moving inward from an outside of the venturi injector.

5. The venturi injector of claim 2, further comprising a collet locking system connected to the water entry port and configured to removably attach the water entry tube to the water entry port.

6. The venturi injector of claim 5, wherein the collet locking system is configured to seat against two outermost steps of the stepped aperture.

7. The venturi injector of claim 5, wherein the collet locking system includes a collet, a lock ring, and an O-ring.

8. The venturi injector of claim 2, further comprising a removable motive throat insert configured to be seated against an innermost step of the stepped aperture.

9. The venturi injector of claim 8, wherein the motive throat insert comprises a top ring end having a surface configured to seat against said innermost step of the stepped aperture, and a bottom end that is narrower than the top ring end and is configured to fit into said central tube.

10. The venturi injector of claim 1,
wherein the water exit port comprises the stepped aperture having at least three steps, each having successively narrow diameters moving inward from an outside of the venturi injector.

11. The venturi injector of claim 1, further comprising a collet locking system connected to the water exit port and configured to removably attach the water exit tube to the water exit port.

12. The venturi injector of claim 11,
wherein the collet locking system is configured to seat against two outermost steps of the stepped aperture.

13. The venturi injector of claim 11,
wherein the collet locking system includes a collet, a lock ring, and an O-ring.

14. The venturi injector of claim 1,
wherein the gas entry port comprises the stepped aperture having at least three steps, each having successively narrow diameters moving inward from an outside of the venturi injector.

15. The venturi injector of claim 1,
wherein the stepped aperture has at least four steps, and
wherein the venturi injector further comprises a cartridge check valve configured to be disposed adjacent to an innermost step of the stepped aperture.

16. The venturi injector of claim 15 further comprising a collet locking system connected to the gas entry port and configured to removably attach the gas transport tube to the gas entry port.

17. The venturi injector of claim 16,
wherein the collet locking system is configured to seat against two outermost steps of the stepped aperture.

18. The venturi injector of claim 16,
wherein the collet locking system includes a collet, a lock ring, and an O-ring.

19. The venturi injector of claim 1,
wherein an outside diameter portion of the water exit port is threaded to accommodate a threaded nut by which the venturi injector is fixable to a housing through an opening in a wall of the housing.

* * * * *